United States Patent [19]

Grass et al.

[11] 4,405,417
[45] Sep. 20, 1983

[54] PROCESS FOR THE MANUFACTURE OF CYCLOHEXENE DERIVATIVES

[75] Inventors: Hansjörg Grass, Muttenz; Reinhard Zell, Rodersdorf, both of Switzerland

[73] Assignee: Hoffmann-La Roche Inc., Nutley, N.J.

[21] Appl. No.: 458,428

[22] Filed: Jan. 17, 1983

[30] Foreign Application Priority Data

Feb. 9, 1982 [CH] Switzerland .................... 784/82

[51] Int. Cl.³ ............................................. C25B 3/00
[52] U.S. Cl. ............................... 204/73 R; 568/378
[58] Field of Search .................. 204/73 R, 59 R; 568/378

[56] References Cited

U.S. PATENT DOCUMENTS 4,193,850  3/1980  Hengartner .................... 204/59 R

FOREIGN PATENT DOCUMENTS 2653838  2/1977  Fed. Rep. of Germany .

OTHER PUBLICATIONS

Widmer et al. Helv. Chim. Acta. 82, V65(3), pp. 958–967.

*Primary Examiner*—John F. Niebling
*Attorney, Agent, or Firm*—Jon S. Saxe; Bernard S. Leon; George M. Gould

[57] ABSTRACT

A process for the manufacture of the novel compound of the formula

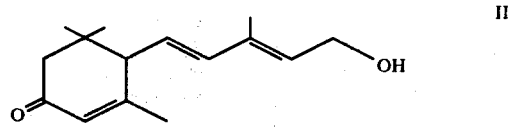

II from the compound of the formula

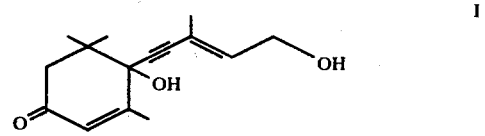

I is described. This process comprises cathodically reducing the compound of formula I in a basic, aqueous-organic solvent mixture.

The compound of formula II is an intermediate in the manufacture of rhodoxanthin or zeaxanthin.

9 Claims, No Drawings

PROCESS FOR THE MANUFACTURE OF CYCLOHEXENE DERIVATIVES

BACKGROUND OF THE INVENTION

The present invention is concerned with a novel process for the manufacture of cyclohexene derivatives. More particularly, the invention is concerned with a process for the manufacture of cyclohexene derivatives which are suitable as intermediates for the manufacture of rhodoxanthin or zeaxanthin, as well as a process for the manufacture of rhodoxanthin or of zeaxanthin itself.

The term zeaxanthin used in this Specification means (3RS,3'RS)-zeaxanthin.

Rhodoxanthin is a naturally occurring carotenoid which can be used, inter alia, as a foodstuff colouring substance. Zeaxanthin, the (3R,3'R)-antipode of which occurs in nature, can also be used as a foodstuff colouring substance (e.g. for egg yolk pigmentation).

Hitherto known syntheses for the manufacture of these two carotenoids require about 10 to 18 steps. Thus, for example, known multistep processes for producing these compounds are described in the following papers:

- H. Mayer et. al. Helv. Chim Acta 50, 1606 (1967);
- J. S. Surmatis et al. Helv. Chim Acta 53, 974 (1970)
- J. D. Surmatis et. al. J. Org. Chem 35 1053 (1970) (describes a 15 to 16 step synthesis of rhodoxanthin)
- P. Karrer et al. Helv Chim Acta 18 477 (1935) (describes the conversion of rhodoxathin to racemic zeaxanthin); and
- R. Kuhn et al. Berichte 66 1319, (1933) (describes the oxidation of dihydrohodoxanthin to rhodoxathin).

DESCRIPTION OF THE INVENTION

The process provided by the present invention comprises cathodically reducing the compound of the formula:

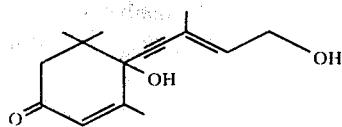

in a basic, aqueous-organic solvent mixture to give the compound of the formula

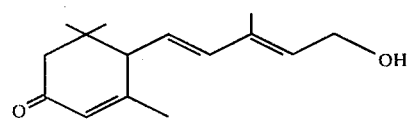

if desired, reacting the compound of formula II, after conversion into a phosphonium salt of the formula

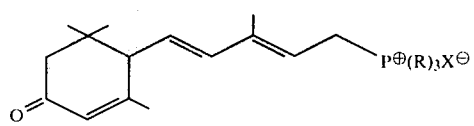

wherein R signifies phenyl and X signifies chlorine, bromine or iodine, with the dialdehyde of the formula

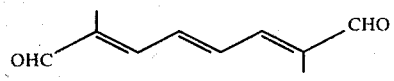

to give the compound of the formula

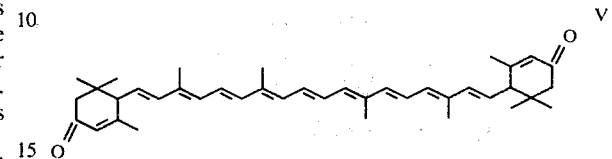

if desired, dehydrogenating the compound of formula V to give rhodoxanthin of the formula

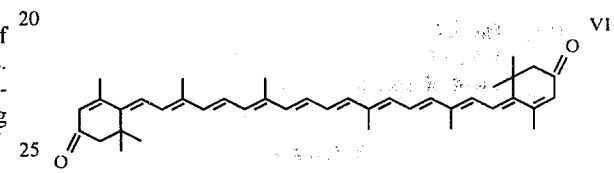

and, if desired, reducing this rhodoxanthin to give zeaxanthin of the formula

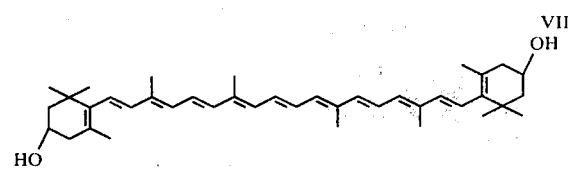

The compound of formula II is novel and is also an object of the present invention.

The conversion of the compound of formula I into the compound of formula II involves a reductive elimination of the angular hydroxy group and simultaneous partial reduction of the triple bond.

The reduction of the compound of formula I can be carried out in undivided or subdivided cells. However, a subdivided cell is preferably used, whereby the subdivision can be carried out with membranes or diaphragms of usual membrane or diaphragm materials such as clay, ceramics, glass (e.g. glass sinter diaphragm) or polymeric compounds (usual polymeric compounds having cation or anion exchange properties, e.g. perfluorinated polymers containing sulfo groups such as NAFION ® DuPont).

The electrodes can have usual forms. For example, the electrodes can be constructed in the form of plates or lattices or as expanded metal. The anode and cathode materials used are not critical.

As cathode materials there are preferably used mercury (e.g. as a mercury sump electrode), lead, cadmium, tin, zinc, graphite, copper, silver, chrome-nickel steel, brass, vanadium, cobalt, platinum, nickel and the like. Lead and graphite are especially preferred cathode materials.

Suitable anode materials are, for example, platinum, graphite, nickel, iron, cobalt, lead, chromium, chrome-nickel steel or copper. Further, dimension-stable anodes [such as, for example, those mentioned n A. Schmidt, Angewandte Elektrochemie, p. 70, Verlag Chemie (1976)], also called metal oxide composite anodes, can also be used. Such composite anodes consist of a carrier of titanium, iron, nickel, copper, graphite, tantalum and the like which is provided with a metal oxide coating (e.g. lead dioxide, ruthenium dioxide or manganese dioxide), whereby an intermediate layer of a carbide or boride of the elements of the IVth and Vth sub-group is applied to the surface of the carrier before the application of the metal oxide coating.

The cathodic reduction of the compound of formula I is carried out in a basic, aqueous-organic solvent mixture consisting of an aqueous electrolyte (aqueous component) and an inert organic solvent (organic component).

As the aqueous electrolyte there can be used an aqueous solution of a base, preferably an inorganic base such as sodium hydroxide, potassium hydroxide, lithium hydroxide, ammonia and the like. Sodium hydroxide is especially preferred. The concentration is not critical. However, the cathodic reduction is generally carried out with about 0.05 N to about 10 N solutions. About 0.1–1 N and especially about 0.1–0.3 N solutions are preferably used. When a dilute solution or ammonia is used as the base a conducting salt can be added in order to improve the conductivity. The conducting salt can be a usual inorganic salt such as sodium chloride, sodium sulphate, potassium choride, potassium bromide, lithium chloride, ammonium chloride and the like or also an organic salt such as for example, tetrabutylammonium hydroxide, tetraethylammonium tosylate or tetrabutylammonium bromide.

The inert organic solvent can be water-miscible or non water-miscible. Example of suitable solvents are lower alcohols (with 1–4 carbon atoms), cyclic ethers, acetone, 1,2-dichloroethane, carbon tetrachloride and the like. Preferred organic solvents are the lower alcohols such as methanol, ethanol, isopropanol and t-butanol and especially the cyclic ethers such as 1,4-dioxan and tetrahydrofuran.

In the case of two-phase solvent mixtures a phase transfer catalyst is conveniently added to the reaction mixture. Suitable phase transfer catalysts are, for example, the tetraalkylammonium salts such as tetramethylammonium tetrafluoroborate, tetraethylammonium tosylate, tetrabutylammonium perchlorate, tetrabutylammonium bromide, tetrakis-decyl-ammonium perchlorate, hexadecyltrimethylammonium bromide and especially the tetraalkylammonium hydroxides such as tetraethylammonium hydroxide, tetrabutylammonium hydroxide and the like. The amount of such compounds depends on the desired conductivity, the solvent mixture used and the like.

The optimum volume ratio electrolyte/organic solvent can differ depending on educt concentration, solvent mixture used and the like. In general, however, it lies between about 6:1 and about 1:5 and preferably between about 6:1 and about 1:1.

The concentration of the starting material of formula I in the reaction mixture used is not critical. It can in general vary between about 0.4% and about 6% (weight/volume).

The temperature at which the reduction of the compound of formula I is carried out is not critical. However, it is limited as regards the upper limit by the boiling point of the reaction mixture. The reduction is preferably carried out at a temperature between room temperature and about 70° C. The reduction can be carried out in the presence or absence of a protective gas atmosphere. The reduction is preferably carried out under an inert gas atmosphere (e.g. nitrogen, argon and the like).

The cathodic reduction of the compound of formula I can be carried out galvanostatically or potentiostatically. The potentiostatic process is preferred.

The requisite potential depends on the reaction mixture and cathode material used and can be determined by measuring the current-potential curves (e.g. by cyclic voltammetry). In general, it lies between about $-1500$ mV and about $-1900$ mV (measured against a saturated calomel electrode).

The current density is not critical. The cathodic reduction is conveniently carried out at a current density of about 2–50 mA/cm$^2$ and preferably about 2–10 mA/cm$^2$.

The cell voltage and the amperage depend on the reaction mixture used, the size of the cell, the current density used and the like and can therefore vary substantially.

In the conversion of the compound of formula II into the phosphonium salt of formula III, the allylic hydroxyl group in the compound of formula II is firstly replaced by halogen. This replacement can be carried out in a manner known per se by means of hydrogen halide (hydrogen chloride, hydrogen bromide or hydrogen iodide) in aqueous solution (e.g. 37%, 48% or 57%). The replacement can be carried out at temperatures between about $-20°$ C. and about $+25°$ C., preferably at about 0° C. As the solvent for this reaction there can be used a solvent which is suitable for such replacement reactions, for example a chlorinated hydrocarbon such as methylene chloride or chloroform and the like.

The conversion of a thus-obtained halide into a phosphonium salt of formula III can be carried out in a manner known per se. The reaction is conveniently carried out using a triarylphosphine, especially triphenylphosphine, in a suitable inert organic solvent such as, for example, a chlorinated hydrocarbon (e.g. methylene chloride or chloroform) or an ester of a lower carboxylic acid containing 1 to 4 carbon atoms (e.g. ethyl formate, ethyl acetate etc). Furthermore, the reaction is preferably carried out under an inert gas atmosphere and at about room temperature or at an elevated temperature. The temperature is, however, of no critical significance in this reaction.

The reaction of a phosphonium salt of formula III with the dialdehyde of formula IV to give the compound of formula V can be carried out in a manner known per se; that is to say, under the conditions which are usual in the case of Wittig reactions. The reaction is conveniently carried out in a chlorinated hydrocarbon such as, for example, methylene chloride or chloroform and in the presence of a base such as, for example, sodium methylate. In this case it is advantageous to add the base to the reaction mixture not all at once, but slowly and continuously.

The dehydrogenation of the compound of formula V to give rhodoxanthin of formula VI can be carried out in a manner known per se; for example, in accordance with the oxidation of dihydrorhodoxanthin to rhodoxanthin which is described by Kuhn and Brockmann in Ber. 66, 1319 (1933).

The reduction of rhodoxanthin of formula VI to give zeaxanthin of formula VII can likewise be carried out in a manner known per se; for example, in accordance with Karrer and Solmssen, Helv. Chim. Acta 18, 477 (1935).

The compound of formula I used as the starting material in the process provided by the present invention is novel and is also an object of the present invention. It can be prepared starting from ketoisophorone of the formula

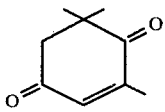

VIII by reaction with the compound of the formula

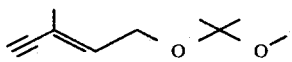

IX

This reaction is conveniently carried out via the lithium or magnesium salt of the compound IX in an inert organic solvent for organometal compounds such as, for example, open or cyclic ethers (e.g. diethyl ether, dioxan end tetrahydrofuran or aromatic hydrocarbons (e.g. benzene, toluene or the like) or also in liquid ammonia. The reaction is preferably carried out at a temperature of about −50° C. to about room temperature. The ketoisophorone used in the reaction must be protected in the 3-position (e.g. in the form of the lithium enolate or as a monoacetal and the like).

The invention is also concerned with all novel compounds, mixtures, processes and uses as herein described.

The following Examples illustrate the process provided by the present invention:

EXAMPLE 1

A glass vessel (H cell) divided into two was used as the reaction vessel. The anode compartment was separated from the cathode compartment by a round polymer membrane (diameter 7 cm). A lead sheet (5.5 cm×7.5 cm) was used as the cathode, a saturated silver/silver chloride electrode (SSE) was used as the reference electrode (in the cathode compartment) and a platinum sheet (2.5 cm×2.5 cm) was used as the anode. Both electrode compartments were provided with a gas inlet tube and the cathode compartment was provided with a magnetic stirrer.

While stirring and introducing nitrogen, 230 ml of 1,4-dioxan, 230 ml of 0.1 N sodium hydroxide and 12.4 g of 4-hydroxy-4-(5-hydroxy-3-methyl-3-penten-1-ynyl)-3,5,5-trimethyl-2-cyclohexen-1-one were added to the cathode compartment and 230 ml of 1,4-dioxan and 230 ml of 0.1 N sodium hydroxide were added to the anode compartment. The mixture was subsequently electrolyzed at a cathode potential of −1550 mV (against SSE) while stirring and introducing nitrogen, an amperage of about 120 mA setting in. The course of the electrolysis was followed continuously by means of thin-layer chromatography. After the amperage had dropped to 10 mA and an amount of current of 17400 Coulomb (90% of theory) had flowed through the cell, the catholyte solution was made acid with 30 ml of 3 N sulphuric acid in a separating funnel $S_1$. Two further separating funnels $S_2$ and $S_3$ were each charged with about 300 ml of semi-saturated sodium chloride solutions. Three 150 ml portions of methylene chloride were passed in succession through the three separating funnels $S_1$–$S_3$. The organic phases were dried over sodium sulphate and filtered. The combined filtrates were concentrated up to constant weight in a rotary evaporator under a water-jet vacuum, there being obtained 12.5 g of a yellow-brown resin which was purified by column chromatography on silica gel. As the eluant there was used firstly methylene chloride and then a methylene chloride/diethyl ether mixture (volume ratio 19:1). The purity of the individual fractions was controlled by means of thin-layer chromatography. The pure fractions were combined and concentrated up to constant weight under a water-jet vacuum at 60° C. There were thus obtained 6.3 g (54%) of 4-(5-hydroxy-3-methyl-1,3-pentadienyl)-3,5,5-trimethyl-2-cyclohexen-1-one in the form of a yellow oil. The structure of this compound was characterized unequivocally by NMR spectroscopy.

The 4-hydroxy-4-(5-hydroxy-3-methyl-3-penten-1-ynyl)-3,5,5-trimethyl-2-cyclohexen-1-one used as the starting material can be prepared as follows:

250 ml of ammonia were condensed in a 750 ml sulphonation flask provided with stirrer, thermometer, ammonia condenser and a 100 ml dropping funnel with pressure balance and gasification headpiece and then treated with 0.1 g of iron (III) nitrate. A total of 3.2 g of lithium wire (0.46 g-atoms) were thereupon added in portions in about 15 minutes. The mixture was further stirred at −40° C. until the reaction to lithium amide was complete (about 20 minutes). Subsequently, there was added dropwise in about 20 minutes while cooling with an acetone dry-ice bath at −40° C. a solution of 77.4 g of acetone methyl 3-methyl-2-penten-4-ynyl acetal in 20 ml of absolute ether, followed by 30.4 g of 2,6,6-trimethyl-2-cyclohexene-1,4-dione in 20 ml of absolute ether. The mixture was stirred at −40° C. until the reaction was complete (about 2.5 hours). 200 ml of absolute ether were now added and subsequently ammonia was driven off with the aid of a warm water bath. As soon as the mixture had reached room temperature, it was cooled further to 0° C. with an ice-bath and hydrolyzed by the dropwise addition of 100 ml of deionized water. For the further working-up, the mixture was rinsed into a 1 liter separating funnel $S_1$ with the aid of 100 ml of ether. Two further 500 ml separating funnels ($S_2$ and $S_3$) were each charged with 200 ml of ether. Thereupon, firstly the aqueous phase from $S_1$ as well as three 100 ml portions of semi-saturated sodium chloride solution were passed in succession and with good intermixing through the three separating funnels $S_1$ to $S_3$. The organic extracts were combined and dried over 50 g of sodium sulphate. Thereupon, the mixture was suction filtered, the drying agent was rinsed on the suction filter with 50 ml of ether and the filtrates were concentrated in a rotary evaporator under a water-jet vacuum at 30° C. The residue was subsequently concentrated up to constant weight in a rotary evaporator with dry-ice condenser under a fine vacuum (about 0.1 mbar) at 65° C. There were thus obtained 62 g (96.8%) of a product in the form of a dark oil.

For the hydrolysis, the foregoing 62 g of product were taken up in 100 ml of acetone and treated dropwise with 50 ml of 3 N sulphuric acid in 15 minutes at 0° C. while stirring and gassing with argon. The black mixture was washed into a 500 ml separating funnel $S_1$ with the aid of 100 ml of ether and then treated with 200 ml of semi-saturated sodium chloride solution and shaken well. Two further 500 ml separating funnels ($S_2$ and $S_3$) were each charged with 200 ml of ether. Thereupon, the aqueous phase from $S_1$ as well as two 100 ml portions of semi-saturated sodium chloride solution were passed in succession with good intermixing through the three separating funnels $S_1$ to $S_3$. The organic phases were combined and dried over 50 g of sodium sulphate. Thereupon, the mixture was suction filtered, the drying agent was rinsed on the suction filter with 50 ml of ether and the filtrates were concentrated up to constant weight in a rotary evaporator under a water-jet vacuum at 30° C. There were thus obtained 49.1 g (99.0%) of 4-hydroxy-4-(5-hydroxy-3-methyl-3-penten-1-ynyl)-3,5,5-trimethyl-2-cyclohexen-1-one in the form of a light brownish oil.

EXAMPLE 2

A thermostatizable H cell was used as the reaction vessel. The anode compartment was separated from the cathode compartment by a round polymer membrane (diameter 4 cm). A lead sheet (3.5 cm × 3.5 cm) was used as the cathode and a platinum wire was used as the anode. The cathode potential was measured against a saturated calomel reference electrode (SCE). Both electrode compartments were provided with a gas inlet tube and a condenser and the cathode compartment was provided with a magnetic stirrer.

While stirring and introducing nitrogen, 45 ml of ethanol, 45 ml of 0.1 N sodium hydroxide and 4.97 g of 4-hydroxy-4-(5-hydroxy-3-methyl-3-penten-1-ynyl)-3,5,5-trimethyl-2-cyclohexen-1-one (prepared in accordance with Example 1) were added to the cathode compartment and 45 ml of ethanol and 45 ml of 0.1 N sodium hydroxide were added to the anode compartment. The mixture was warmed to a constant temperature of 65° C. and then electrolyzed at a cathode potential of −1900 mV (against SCE) while stirring and gassing with nitrogen, an amperage of 160 mA setting in. The course of the electrolysis was followed continuously by means of thin-layer chromatography. After the amperage had dropped to 80 mA and an amount of current of 6330 Coulomb (80% of theory) had flowed through the cell, the electrolysis was interrupted, although the educt had still not reacted completely. The catholyte solution was subsequently diluted with 200 ml of semi-saturated sodium chloride solution in a separating funnel $S_1$. Two further separating funnels $S_2$ and $S_3$ were each charged with about 150 ml of semi-saturated sodium chloride solution. Three 150 ml portions of methylene chloride were passed in succession through the three separating funnels $S_1-S_3$ and then the organic phases were dried over sodium sulphate and filtered. The combined filtrates were concentrated up to constant weight in a rotary evaporator at 60° C. under a water-jet vacuum. There was thus obtained a brown oil which was purified by chromatography on a column of silica gel. A diethyl ether/hexane mixture was used as the eluant. The purity of the individual fractions was controlled by means of thin-layer chromatography. The pure fractions were combined (the remaining fractions were not worked-up) and concentrated up to constant weight under a water jet vacuum at 60° C. There were thus obtained 1.8 g (39%) of 4-(5-hydroxy-3-methyl-1,3-pentadienyl)-3,5,5-trimethyl-2-cyclohexen-1-one in the form of a yellow oil. The structure of this compound was characterized unequivocally by microanalysis, IR, MS and NMR spectra. The foregoing process conditions are not optimized.

EXAMPLE 3

A thermostatizable H cell was used as the reaction vessel. The anode compartment was separated from the cathode compartment by a round polymer membrane (diameter 4 cm). A graphite electrode (5.5 cm × 7.5 cm) was used as the cathode and a platinum wire was used as the anode. The cathode potential was measured against a saturated calomel reference electrode (SCE). Both electrode compartments were provided with a gas inlet tube and a condenser and the cathode compartment was provided with a magnetic stirrer.

While stirring and introducing nitrogen, 250 ml of tetrahydrofuran, 250 ml of 0.2 N sodium hydroxide and 5.42 g of 4-hydroxy-4-(5-hydroxy-3-methyl-3-penten-1-ynyl)-3,5,5-trimethyl-2-cyclohexen-1-one (prepared in accordance with Example 1) were added to the cathode compartment and 250 ml of tetrahydrofuran and 250 ml of 0.2 N sodium hydroxide were added to the anode compartment. The mixture was warmed to a constant temperature of 55° C. and then electrolyzed at a cathode potential of −1600 mV (against SCE) while stirring and gassing with nitrogen, an amperage of 250 mA setting in. The course of the electrolysis was followed continuously by means of thin-layer chromatography. After the amperage had dropped to 120 mA and an amount of current of 12700 Coulomb (151% of theory) had flowed through the cell, the electrolysis was interrupted. The catholyte solution and the anolyte solution were subsequently combined and made acid with 50 ml of 3 N sulphuric acid in a separating funnel $S_1$. Two further separating funnels $S_2$ and $S_3$ were each charged with about 1 l of dilute sodium chloride solution. Three 300 ml portions of methylene chloride were passed in succession through the three separating funnels $S_1-S_3$. The organic phases were dried over sodium sulphate and filtered. The combined filtrates were concentrated up to constant weight in a rotary evaporator under a water-jet vacuum, there being obtained 5.7 g of a brown resin which was purified by column chromatography on silica gel. As the eluant there was used firstly methylene chloride and subsequently various methylene chloride/diethyl ether mixtures (volume ratio: 49:1, 19:1, 9:1). The purity of the individual fractions was controlled by means of thin-layer chromatography. The pure fractions were combined and concentrated up to constant weight under a water-jet vacuum at 60° C. There were thus obtained 2.75 g (54%) of 4-(5-hydroxy-3-methyl-1,3-pentadienyl)-3,5,5-trimethyl-2-cyclohexen-1-one in the form of a yellow oil. The structure of this compound was characterized unequivocally by microanalysis, NMR, IR and MS spectra.

EXAMPLE 4

Experiments A-N listed in Table 1 were carried out in an analogous manner to the methods described in Examples 1-3. A cell subdivided into anode and cathode compartments by a glass membrane was used as the reaction vessel. Experiments F, J, K and L were carried out potentiostatically and the remaining experiments were carried out galvanostatically. The applied potential (against a saturated calomel electrode) amounted to −1700 mV in experiments F and J and to −1600 mV in experiments K and L. Lead was used as the anode material for experiments D and G and platinum was used as the anode material for experiments M and N; the remaining experiments were carried out with a lead dioxide/titanium composite anode. In all experiments there were used in each case the same amounts of catholyte and anolyte. In experiments B–G, M and N anolyte and catholyte had, moreover, the same composition. In experiments A and H–L the use of an organic solvent in the anode compartment was, however, waived and as the anolyte there was used only the aqueous solution given in the Table as the electrolyte. Further, in experiment K 2 g of tetrabutylammonium hydroxide were added as the phase transfer catalyst. The amount of 4-hydroxy-4-(5-hydroxy-3-methyl-3-penten-1-ynyl)-3,5,5-trimethyl-2-cyclohexen-1-one used was 0.3 g in experiments F and K, 0.4 g in experiment M and 0.5 g in each of the remaining experiments. All experiments were carried out under a nitrogen atmosphere and at room temperature.

All experiments gave the desired product, 4-(5-hydroxy-3-methyl-1,3-pentadienyl)-3,5,5-trimethyl-2-cyclohexen-1-one. (Detection by means of thin-layer chromatography). The mixtures were, however, not worked-up and the process conditions were not optimized.

TABLE 1

| Experiment | Cathode | Catholyte Electrolyte | Catholyte Organic solvent | Amperage [mA/cm$^2$] |
|---|---|---|---|---|
| A | Pb | 35 ml 1M NH$_3$/NH$_4$Cl | 35 ml CH$_3$OH | 8 |
| B | Pb | 50 ml 0.5N NaOH | 25 ml t-butanol | 4 |
| C | Pb | 12.5 ml 6N NaOH | 62.5 ml CH$_3$OH | 5 |
| D | Hg | 60 ml 0.5N NaOH | 15 ml isopropanol | 4 |
| E | Brass | 60 ml 0.5N NaOH | 15 ml CH$_3$OH | 4 |
| F | Pt | 35 ml 1N NaOH | 35 ml dioxan | About 3 |
| G | Cd | 35 ml 0.5N NaOH | 35 ml acetone | 25 |
| H | C | 60 ml 2N NaOH | 10 ml t-butanol | 50 |
| I | Sn | 35 ml 1N NaOH | 35 ml tetrahydrofuran | 20 |
| J | Cu | 35 ml 0.1N NaOH | 35 ml dioxan | About 6.4 |
| K | Pb | 45 ml 0.5N NaOH | 25 ml ClCH$_2$CH$_2$Cl | About 3 |
| L | Ni | 35 ml 0.1N NaOH | 35 ml dioxan | About 8 |
| M | Pb | 35 ml 1N LiOH | 35 ml dioxan | 7 |
| N | Pb | 35 ml 1N KOH | 35 ml dioxan | 7 |

EXAMPLE 5

(A) 46.6 g (0.2 mol) of 4-(5-hydroxy-3-methyl-1,3-pentadienyl)-3,5,5-trimethyl-2-cyclohexen-1-one (prepared in accordance with any one of Examples 1–3) dissolved in 200 ml of methylene chloride were placed in a 1.5 liter sulphonation flask provided with stirrer, thermometer, 500 ml dropping funnel and pressure balance and an apparatus for inert gasification and treated dropwise with a total of 124 ml of 37% hydrochloric acid at −5° C. to 0° C. in about 20 minutes while stirring well and gassing with argon. Thereupon, the mixture was stirred for a further 15 minutes at 0° C. until the reaction was complete. Subsequently, the dark mixture was transferred into a 1 liter separating funnel S$_1$ with the aid of 200 ml of methylene chloride. Two further 1 liter separating funnels (S$_2$ and S$_3$) were each charged with 250 ml of saturated sodium bicarbonate solution. Thereupon, the lower organic phase from S$_1$ as well as two 250 ml portions of 250 ml of methylene chloride were passed with good intermixing through the three separating funnels S$_1$ to S$_3$. The organic phases were thereupon combined, dried over 50 g of sodium sulphate, suction filtered and the drying agent was rinsed on the suction filter with 50 ml of methylene chloride. The filtrate was then concentrated to a volume of about 100 ml in a rotary evaporator under a water-jet vacuum at 30° C. (bath temperature).

(B) A solution of 52.4 g (0.2 mol) of triphenylphosphine in 100 ml of methylene chloride was placed in a 2.5 liter sulphonation flask provided with stirrer, thermometer, 250 ml dropping funnel with pressure balance and an apparatus for inert gasification. With stirring and inert gasification there was then added dropwise within about 10 minutes the methylene chloride solution obtained in accordance with paragraph (A). The dark solution obtained was subsequently stirred at room temperature for a further 21 hours and then concentrated to a volume of about 200 ml in a rotary evaporator under a water-jet vacuum at 30° C. (bath temperature). Subsequently, 850 ml of ethyl acetate were added dropwise in about 30 minutes with stirring and argon gasification, crystallization soon beginning. The resulting suspension was then stirred at room temperature for 24 hours and in ice for 2 hours, suction filtered, the product on the suction filter was washed thoroughly with two 100 ml portions of ethyl acetate and then dried up to constant weight in a drying oven under a water-jet vacuum at 40° C. The crystals were subsequently recrystallized from methylene chloride/ethyl acetate and there were obtained 63.3 g (61.7%) of [3-methyl-5-(2,6,6-trimethyl-4-oxo-2-cyclohexen-1-yl)-2,4-pentadienyl]triphenyl- phosphonium chloride of melting point 164°–166° C.

EXAMPLE 6

(A) 2.08 g (8.9 mmol) of 4-(5-hydroxy-3-methyl-1,3-pentadienyl)-3,5,5-trimethyl-2-cyclohexen-1-one (prepared in accordance with any one of Examples 1–3) dissolved in 10 ml of methylene chloride was placed in a 50 ml multi-necked round flask provided with stirrer, thermometer, 10 ml dropping funnel with pressure balance and an apparatus for inert gasification and treated dropwise at −15° C. during 10 minutes with 4.8 ml of 63% hydrobromic acid. Thereafter, the mixture was stirred at −15° C. for about a further 30 minutes. Subsequently, the dark mixture was transferred into a 50 ml separating funnel S$_1$ with the aid of 25 ml of methylene chloride. Two further 50 ml separating funnels (S$_2$ and S$_3$) were each charged with 25 ml of saturated sodium bicarbonate solution. Now, the lower organic phase from S$_1$ as well as two 25 ml portions of methylene chloride were passed with good intermixing through the three separating funnels S$_1$ to S$_3$. The organic phases were combined, dried over 25 g of sodium sulphate, then suction filtered, the drying agent was rinsed on the suction filter with 25 ml of methylene chloride and the filtrate was concentrated to a volume of about 10 ml in a rotary evaporator under a water-jet vacuum at 30° C. (bath temperature).

(B) 2.89 g (11 mmol) of triphenylphosphine in 10 ml of methylene chloride were placed in a 50 ml round flask provided with stirrer, thermometer, 10 ml dropping funnel with pressure balance and an apparatus for inert gasification. With stirring and gassing with argon there was then added dropwise in about 10 minutes the methylene chloride solution in accordance with paragraph (A). The dark solution was subsequently stirred at room temperature for about a further 2 hours and then concentrated to a volume of about 20 ml in a rotary evaporator under a water-jet vacuum at 30° C. (bath temperature). Subsequently 100 ml of ethyl acetate were added dropwise in about 1 hour with stirring and argon gasification. Thereupon, the suspension was seeded, stirred at room temperature for 24 hours and in ice for 2 hours and then suction filtered. The residue on the suction filter was washed thoroughly with two 25 ml portions of ethyl acetate and then dried up to constant weight in a drying oven under a water-jet vacuum at 40° C. There were obtained 4.2 g (84.3%) of [3-methyl-5-(2,6,6-trimethyl-4-oxo-2-cyclohexen-1-yl)-2,4-pentadienyl]triphenylphosphonium bromide of melting point 168°–170° C.

EXAMPLE 7

(A) 103 g (0.20 mol) of [3-methyl-5-(2,6,6-trimethyl-4-oxo-2-cyclohexen-1-yl)-2,4-pentadienyl]triphenylphosphonium chloride and 13.1 g (79.8 mmol) of 2,7-dimethyl-octatriene-(2,4,6)-dial-(1,8) dissolved in 800 ml of methylene chloride were placed in a 1.5 liter sulphonation flask provided with stirrer, thermometer, 50 ml dropping funnel with pressure balance and an apparatus for inert gasification. While stirring, gassing with argon and cooling at −20° C. there were now added dropwise in the course of 2 hours 46 ml of 10% sodium methylate solution. The mixture was subsequently stirred at 0° C. for a further 2 hours. The reaction was quenched by the addition of 12 ml of glacial acetic acid. Three 2 liter separating funnels $S_1$ to $S_3$ were each charged with 500 ml of saturated sodium chloride solution. Then, firstly the reaction solution and then two 500 ml portions of methylene chloride were passed with vigorous intermixing through the three separating funnels $S_1$ to $S_3$. The organic extracts were combined, dried over 100 g of sodium sulphate, suction filtered and the drying agent was rinsed on the suction filter twice with 200 ml of methylene chloride.

(B) The filtrate obtained in accordance with paragraph (A) was added to a 1.5 liter sulphonation flask provided with stirrer, thermometer, 250 ml dropping funnel with pressure balance and apparatus for inert gasification, as well as a distillation headpiece. While stirring and heating (120° C.) and under argon, the solution was concentrated at normal pressure to a volume of about 500 ml. Then, with continuous distillation at a constant volume of about 500 ml there were added dropwise about 1.8 l of methanol until the boiling point of 63° C. had been reached. A product crystallized out during this procedure. The distillation headpiece was subsequently replaced by a reflux condenser and the suspension was stirred at reflux for 3 days. The mixture was then cooled to −20° C. and suction filtered. The crystals were washed thoroughly on the suction filter with three 100 ml portions of methanol (at −20° C.) with argon gasification, sucked dry and dried up to constant weight in a drying oven under a water-jet vacuum at 30° C. There were obtained 32 g (71%) of 1,18-bis(4-oxo-2,6,6-trimethyl-2-cyclohexen-1-yl)-3,7,12,16-tetramethyl-1,3,5,7,9,11,13,15,17-octadecanonaene of melting point 185°–187° C.

In a manner analogous to the foregoing, this compound can also be prepared starting from [3-methyl-5-(2,6,6-trimethyl-4-oxo-2-cyclohexen-1-yl)-2,4-pentadienyl]triphenylphosphonium bromide.

EXAMPLE 8

(A) 11.3 g (20 mmol) of 1,18-bis(4-oxo-2,6,6-trimethyl-2-cyclohexen-1-yl)-3,7,12,16-tetramethyl-1,3,5,7,9,11,13,15,17-octadecanonaene were dissolved in 200 ml of pyridine at 70° C. under argon in a 500 ml multi-necked flask provided with a magnetic stirring core, 50 ml dropping funnel and thermometer, the solution was cooled to room temperature, stirred at 0° C. with access of air for 20 minutes and then treated dropwise during 10 minutes with 50 ml of a 1 N ethanolic potassium hydroxide solution. The mixture was then stirred for a further 30 minutes in ice and for 1.5 hours at room temperature and with free access of air. The solution was then transferred into a 1 liter separating funnel $S_1$ with the aid of 200 ml of methylene chloride which contained 400 ml of a 5% sodium chloride solution. Two further 1 liter separating funnels ($S_2$ and $S_3$) were each charged with 500 ml of 3 N hydrochloric acid. Now, the lower organic phase from $S_1$ as well as three 200 ml portions of methylene chloride were passed with good intermixing through the three separating funnels ($S_1$ to $S_3$). The organic extracts were washed with 400 ml of deionized water and 400 ml of 2% sodium bicarbonate solution, dried over 100 ml of sodium sulphate and suction filtered. The drying agent was rinsed on the suction filter with two 200 ml portions of methylene chloride and the filtrate was concentrated to a volume of about 100 ml on a rotary evaporator under a water-jet vacuum at 30° C.

(B) The methylene chloride solution (100 ml) obtained in accordance with paragraph (A) was added to a 350 ml sulphonation flask provided with stirrer, thermometer, 100 ml dropping funnel with pressure balance and apparatus for inert gasification as well as a distillation headpiece. With stirring and distillation, the mixture was concentrated at normal pressure up to a residual volume of about 100 ml. While maintaining this volume deionized water was subsequently added dropwise until the boiling point had reached 93° C. (bath temperature=130° C.). The resulting sticky mass was then stirred at reflux for 48 hours, cooled to room temperature and subsequently dissolved with the aid of about 200 ml of methylene chloride. After the separation of the phases in a 500 ml separating funnel, the organic phase was dried over 25 g of sodium sulphate and suction filtered. The drying agent was rinsed on the suction filter with two 100 ml portions of methylene chloride and the filtrate was concentrated to a volume of about 50 ml on a rotary evaporator under a water-jet vacuum at 30° C. This solution was treated with 150 ml of ethyl acetate, whereupon the mixture was concentrated to a volume of about 50 ml in a rotary evaporator under a water-jet vacuum at 40° C. (bath temperature). In so doing, product began to crystallize out. The suspension was subsequently stirred at 0° C. for a further 2 hours and then suction filtered. The crystals on the suction filter were washed thoroughly with two 50 ml portions of 50 ml of ethyl acetate and then dried up to constant weight in a drying oven under a water-jet vacuum at 30° C. There were obtained 6.3 g (56%) of rhodoxanthin of melting point 208°–210° C.

What is claimed is:

1. A process which comprises cathodically reducing the compound of the formula

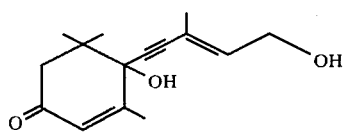
I in a basic, aqueous-organic solvent mixture to give the compound of the formula.

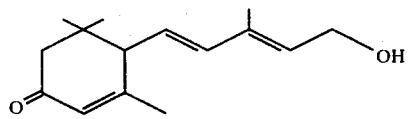
II

2. A process according to claim 1, wherein the cathodic reduction of the compound of formula I is carried out in a subdivided cell.

3. A process according to claim 1, wherein the aqueous component of the aqueous-organic solvent mixture is an aqueous solution of an inorganic base, selected from sodium hydroxide, potassium, hydroxide, lithium hydroxide or ammonia.

4. A process according to claim 3, wherein sodium hydroxide is used as the aqueous component of the aqueous-organic solvent mixture.

5. A process according to claim 1, wherein the organic component of the aqueous-organic solvent mixture is selected from an alcohol containing 1 to 4 carbon atoms or a cyclic ether.

6. A process according to claim 5, wherein the organic component of the aqueous-organic solvent mixture is a cyclic ether, selected from 1,4-dioxan or tetrahydrofuran.

7. A process according to claim 1, wherein the cathodic reduction is carried out in an aqueous-organic solvent mixture whose volume ratio aqueous component/organic component is about 6:1 to about 1:5.

8. A process according to claim 1, wherein the cathodic reduction is carried out at a temperature between room temperature and the boiling temperature of the reaction mixture.

9. A process according to claim 1, wherein lead or graphite is used as the cathode material.

* * * * *